(12) United States Patent
Okuda

(10) Patent No.: US 9,581,566 B2
(45) Date of Patent: Feb. 28, 2017

(54) BIOLOGICAL SAMPLE MEASUREMENT DEVICE

(71) Applicant: PANASONIC HEALTHCARE HOLDINGS CO., LTD., Minato-ku, Tokyo (JP)

(72) Inventor: Eiji Okuda, Ehime (JP)

(73) Assignee: Panasonic Healthcare Holdings Co., Ltd., Minato-Ku, Tokyo (JP)

( * ) Notice: Subject to any disclaimer, the term of this patent is extended or adjusted under 35 U.S.C. 154(b) by 0 days.

(21) Appl. No.: 14/370,215

(22) PCT Filed: Jan. 11, 2013

(86) PCT No.: PCT/JP2013/000078
§ 371 (c)(1),
(2) Date: Jul. 1, 2014

(87) PCT Pub. No.: WO2013/105509
PCT Pub. Date: Jul. 18, 2013

(65) Prior Publication Data
US 2014/0379274 A1    Dec. 25, 2014

(30) Foreign Application Priority Data

Jan. 13, 2012 (JP) ................................. 2012-005001
Nov. 5, 2012 (JP) ................................. 2012-243345

(51) Int. Cl.
*G01N 33/66* (2006.01)
*G01N 27/416* (2006.01)
*G01N 33/487* (2006.01)

(52) U.S. Cl.
CPC .... *G01N 27/4163* (2013.01); *G01N 33/48771* (2013.01); *G01N 33/66* (2013.01)

(58) Field of Classification Search
CPC ..................... G01N 27/4163; G01N 33/48771; G01N 33/66
(Continued)

(56) References Cited

U.S. PATENT DOCUMENTS 5,438,271 A    8/1995  White et al.
5,502,396 A    3/1996  Desarzens et al.
(Continued)

FOREIGN PATENT DOCUMENTS

EP        1586889 A2    10/2005
JP     H07-167812 A     7/1995
(Continued)

OTHER PUBLICATIONS

International Search Report of Int'l Appln. No. PCT/JP2013/000078 issued on Mar. 5, 2013.
(Continued)

*Primary Examiner* — Sam P Siefke
(74) *Attorney, Agent, or Firm* — Shinjyu Global IP

(57) ABSTRACT

A biological sample measurement device comprising a main body case including a sensor mounting component; a measurement component including an input side; a controller connected to the measurement component, the controller including a measurement preparation mode and a measurement mode, the controller configured to determine whether there is an abnormality in the measurement component; a memory component connected to the controller; a switching component connected to the input side of the measurement component, a first reference resistor, and to the sensor mounting component; the switching component configured to switch between at least two states.

4 Claims, 5 Drawing Sheets

(58) Field of Classification Search
  IPC .................. G01N 27/4163,33/48771, 33/66
  See application file for complete search history.

(56) References Cited

U.S. PATENT DOCUMENTS

| | | |
|---|---|---|
| 7,776,194 B2 | 8/2010 | Kawase et al. |
| 2005/0230248 A1 | 10/2005 | Kawase et al. |

FOREIGN PATENT DOCUMENTS

| | | |
|---|---|---|
| JP | 2003-515122 A | 4/2003 |
| JP | 2003-215122 A | 7/2003 |
| JP | 2008-527341 A | 7/2008 |
| JP | 2010-008121 A | 1/2010 |
| JP | 2010-230525 A | 10/2010 |
| JP | 2011-027756 A | 2/2011 |
| JP | 2011-143988 A | 7/2011 |
| WO | 01/36934 A2 | 5/2001 |
| WO | 01/36934 A3 | 5/2001 |
| WO | 2006/074927 A1 | 7/2006 |

OTHER PUBLICATIONS

European Search Report from the corresponding European Patent Application No. 13735998.0 issued on Apr. 23, 2015.

BIOLOGICAL SAMPLE MEASUREMENT DEVICE

PRIORITY

This application claims priority to International Application PCT/JP2013/000078, with an international filing date of Jan. 11, 2013 which claims priority to Japanese Patent Application No. JP2012-005001 filed on Jan. 13, 2012 and Japanese Patent Application No. JP2012-243345 filed on Nov. 5, 2012. The entire disclosures of International Application PCT/JP2013/000078, Japanese Patent Application No. JP2012-005001, and Japanese Patent Application No. JP2012-243345 are hereby incorporated herein by reference.

TECHNICAL FIELD

The present invention relates to a biological sample measuring device that measures biological information, such as blood glucose levels from blood.

BACKGROUND

A conventional biological sample measuring device comprised a main body case having a sensor mounting component, a measurement component connected to the sensor mounting component, a controller connected to the measurement component, and a memory component connected to the controller.

A method in which a control liquid or a management chip is used to determine whether or not there is an abnormality in a biological sample measurement device has been proposed as a method for maintaining the measurement accuracy of the biological sample measurement device (see Patent Literature 1: Japanese Laid-Open Patent Application 2003-215122, for example).

However, a conventional biological sample measurement device was inconvenient to use in the following respects.

When it was determined whether or not there was an abnormality in a conventional biological sample measurement device, the determination was performed by mounting a dedicated management chip to the sensor mounting component, and it was confirmed from this determination that there was no abnormality in the biological sample measurement device. After this, a sensor for measurement was mounted to the sensor mounting component, and the measurement of a biological sample was carried out.

That is, prior to the measurement of the biological sample, a dedicated management chip had to be mounted to the sensor mounting component to determine whether or not there was an abnormality in the biological sample measurement device, and this made the device less convenient to use.

SUMMARY

The biological sample measurement device of the present invention comprises a main body case including a sensor mounting component, a measurement component connected to the sensor mounting component, a controller connected to the measurement component, a detector configured to detect a mounting of a sensor to the sensor mounting component connected to the controller, and a memory component connected to the controller. The input side of the measurement component is connected to a switching component configured to switch between an open state, connection to the sensor mounting component, and connection to a reference resistor. The controller has a measurement preparation mode and a measurement mode, and in the measurement preparation mode, the controller performs Check 01 and Check 02 and determines whether there is an abnormality in the measurement component. The controller connects the input side of the measurement component to the sensor mounting component for the measurement mode when the controller determines that there is no abnormality in the measurement preparation mode.

Check 01: In a state where the input side of the measurement component is connected by the switching component to the reference resistor, the controller finds a first measurement value and determines whether or not the first measurement value is within a first reference range stored in the memory component.

Check 02: In a state where the switching component puts the input side of the measurement component in the open state, a second measurement value is found, and it is determined whether or not the second measurement value is within a second reference range stored in the memory component.

Specifically, with the biological sample measurement device of the present invention, the measurement preparation mode is started when the detector detects the mounting of a sensor to the sensor mounting component, and in this measurement preparation mode, the controller finds two measurement values by performing measurement in two states: the open state and a state in which the input side of the measurement component is connected to the reference resistor. It is then determined whether or not these two measurement values are within a reference range set at the time of manufacture, and it is confirmed that the present characteristics of the measurement component are still the same as at the time of manufacture, that is, that there is no abnormality. The controller connects the input side of the measurement component to the sensor mounting component for the measurement mode when the controller determines that there is no abnormality in the measurement preparation mode.

Consequently, it can be determined that there is currently no abnormality in the measurement component before the actual measurement is performed.

Since it can be determined whether or not there is an abnormality in the biological sample measurement device with a sensor mounted to a sensor mounting component and therefore without having to take time to mount a dedicated management chip ahead of time as was done in the past, the present invention provides a biological sample measurement device that is more convenient to use.

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

First Embodiment

The biological sample measurement device in a first embodiment of the present invention will now be described through reference to the drawings.

Figure 1:
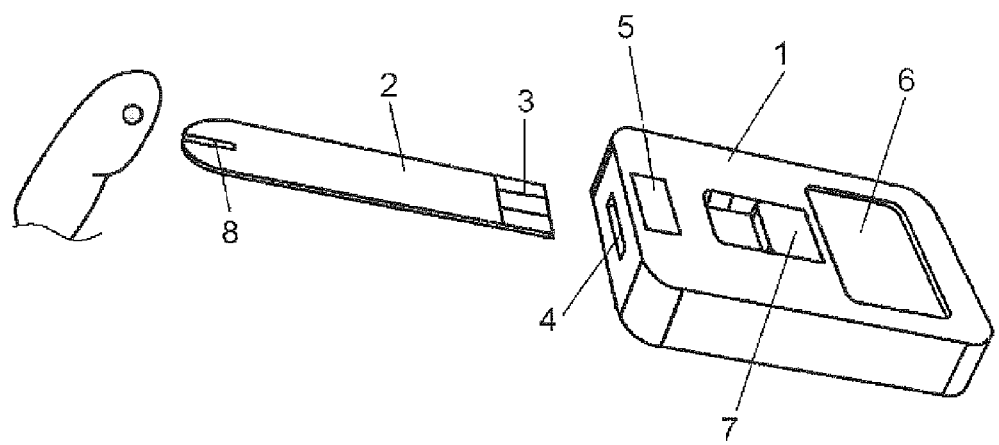
FIG. 1 is an oblique view of a method for using the biological sample measurement device in a first embodiment of the present invention.

As shown in FIG. 1, a main body case 1 of a measurement device that is an example of a biological sample measurement device for measuring blood glucose levels from blood, for example, is formed in a substantially rectangular shape. A sensor mounting component 4, into which is inserted a connection terminal 3 of a blood glucose level sensor 2 (an example of a sensor), is provided on the distal end side of the main body case 1. A power button 5 for turning power on and off to the measurement device, a display component 6 for displaying measurement results and so forth, and an eject lever 7 for removing the blood glucose level sensor 2 from the main body case 1 are provided on the upper face of the main body case 1.

Figure 2:
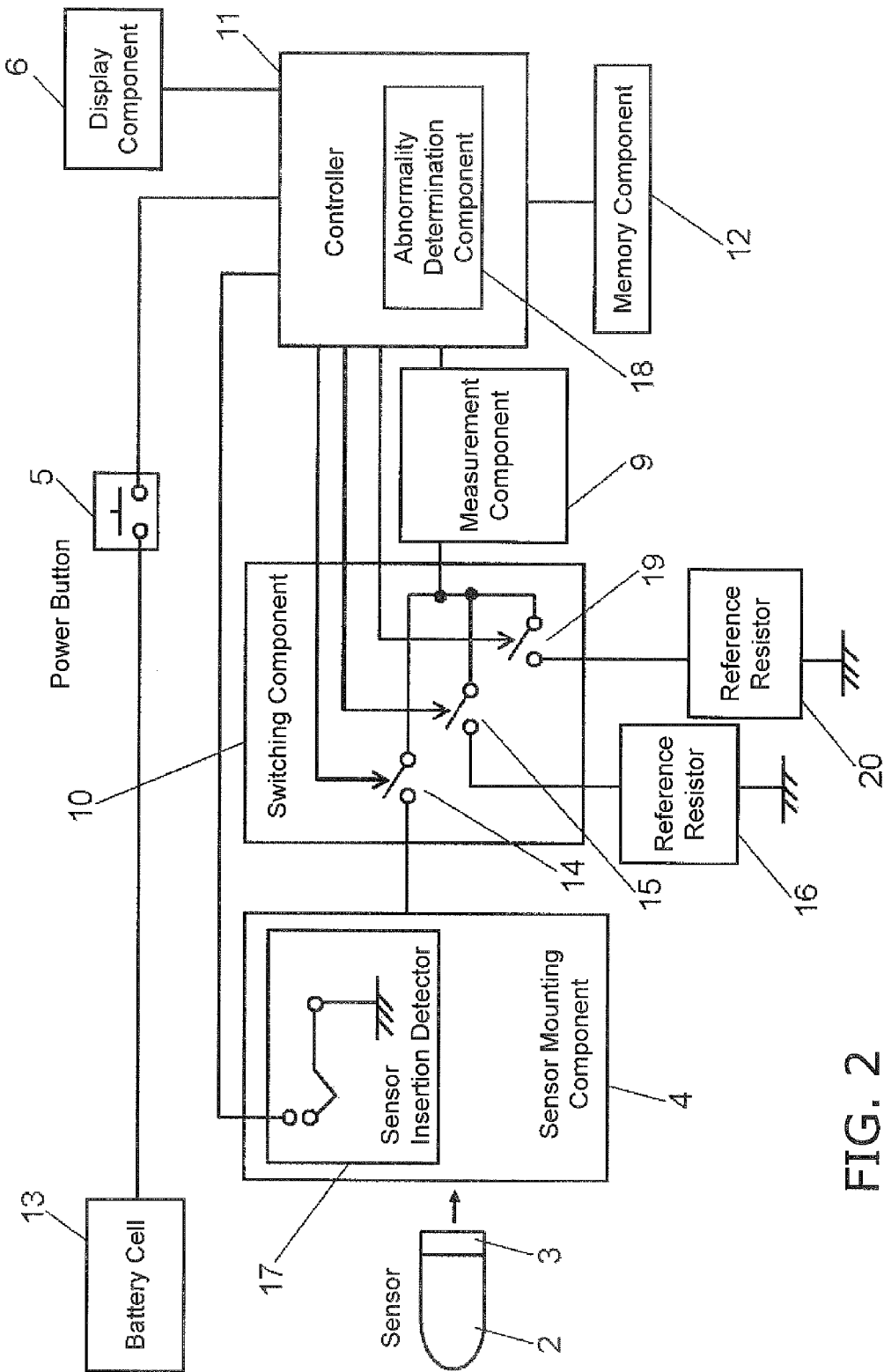
FIG. 2 is a control block diagram of the biological sample measurement device in the first and second embodiments of the present invention.

That is, if the connection terminal 3 of the blood glucose level sensor 2 is mounted to the sensor mounting component 4, and blood is deposited in this state on a deposition component 8 on the distal end side of the blood glucose level sensor 2, the blood glucose level at that point will be measured by a measurement component 9 in FIG. 2, and displayed on the display component 6.

Figure 3:
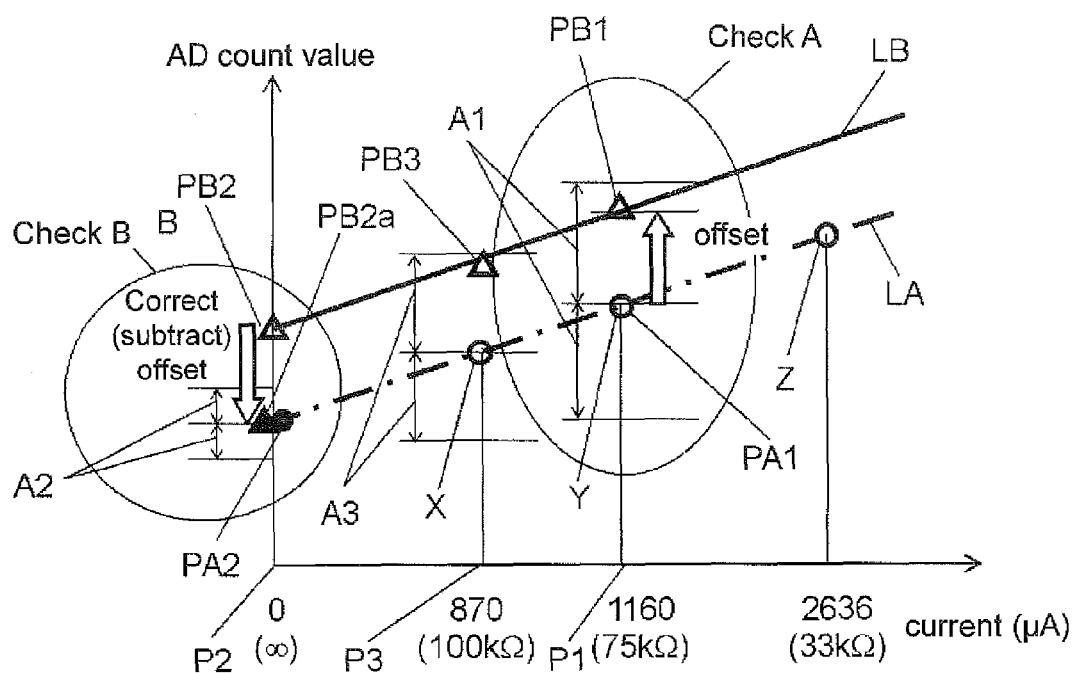
FIG. 3 is a characteristic graph of measurement values obtained with the biological sample measurement device in the first and second embodiments of the present invention.

FIG. 2 is an electrical control block diagram of the measurement device. The sensor mounting component 4 is connected to the measurement component 9 via a switching component 10, and this measurement component 9 is connected to a controller 11. This controller 11 is connected to a memory component 12. This memory component 12 stores reference values PA1 and PA2, and a threshold A1 for the reference value PA1 and a threshold A2 for the reference value PA2, from the time of manufacture, as shown in FIG. 3. The controller 11 is connected to the display component 6, and is also connected to a battery cell 13 via the power button 5.

The sensor mounting component 4 is connected via a switch 14 to the input side of the measurement component 9, and one side of a reference resistor 16 is connected via a switch 15 to this input side. The other side of this reference resistor 16 is grounded.

The switch 14 and the switch 15 constitute the switching component 10 in this embodiment, and are each connected to the controller 11 and are switched on and off by the controller 11. The controller 11 has a measurement preparation mode in which preparation for measurement is carried out, and a measurement mode in which the measurement of a blood glucose level is carried out.

A sensor insertion detector 17 is provided inside the sensor mounting component 4 and is connected to the controller 11.

In this embodiment, before actual measurement of a blood glucose level is started, it is determined in the measurement preparation mode of the controller 11 whether or not there is an abnormality in the measurement component 9.

More specifically, the controller 11 performs measurement at two points for the sake of evaluation, and finds a characteristic line LB (shown in FIG. 3) indicating the measurement characteristics of the measurement component 9 from the measurement values at these two points. Then, the deviation and the difference in slope between the current characteristic line LB and a characteristic line LA at the time of manufacture (shown in FIG. 3) are determined at the two points where measurement was performed for the sake of evaluation.

The evaluation at these two points is used to confirm that the present characteristics of the measurement component 9 are still the same as at the time of its manufacture, that is, that there is no abnormality in the measurement component 9.

This will now be described in detail through reference to FIGS. 2 to 4.

When a blood glucose level is to be measured, the user presses the power button 5 to turn on the power to the measurement device (step S1 in FIG. 4), and mounts the connection terminal 3 of the blood glucose level sensor 2 to the sensor mounting component 4. The sensor insertion detector 17 then detects the insertion of the blood glucose level sensor 2 and notifies the controller 11 (step S2 in FIG. 4).

The control of the power to the measurement device may be such that the power is turned on when the sensor insertion detector 17 detects the insertion of the blood glucose level sensor 2.

The controller 11 goes into measurement preparation mode and starts determining whether or not there is an abnormality in the measurement component 9. This determination of whether or not there is an abnormality will first be described through reference to FIG. 3.

As is well known, a blood glucose level is measured by allowing blood to react with a reagent (not shown) at the deposition component 8 of the blood glucose level sensor 2, converting its reaction current into voltage with a current-voltage circuit (not shown), and converting this voltage into a digital AD count value with an AD conversion circuit (not shown). The blood glucose level is calculated by finding the current value corresponding to this AD count value (the value serving as the basis for calculating the blood glucose level). In FIG. 3, the vertical axis is the AD count value, and the horizontal axis is the current value (the value serving as the basis for calculating the blood glucose level).

At the time of manufacture, the measurement device is tested by measuring with three resistors, such as 100 kΩ, 75 kΩ, and 33 kΩ, instead of the blood glucose level sensor 2, and a value is determined for each (the AD count values, or more specifically, three points for the AD count values X, Y, and Z in the circles in FIG. 3). An approximation line found from the values at these three points (the AD count values X, Y, and Z) is termed the characteristic line LA of the measurement component 9 at the time of its manufacture (indicated by a dashed-dotted line in FIG. 3). 75 kΩ is a value corresponding to a standard blood glucose level (such as 90 mg/dL) when the blood glucose level sensor of this embodiment is used to measure a healthy subject.

In actual measurement, the measurement device uses the characteristic line LA for the measurement component 9 to convert the AD count values into current values, and the controller 11 performs correction such as temperature correction, and calculates the blood glucose level.

In this embodiment, measurement for the sake of evaluation is performed at two points, namely, a reference point P1 (75 kΩ) and a reference point P2 (∞Ω, that is, when the input side of the measurement component 9 is in an open state), prior to actual measurement, and whether or not there is an abnormality in the measurement component 9 is determined from these two points (the reference point P1 and the reference point P2).

Therefore, at the time of manufacture, the measurement value at the reference point P1 (75 kΩ) is set as the reference value PA1 (=AD count value Y), the measurement value at the reference point P2 (∞Ω) is set as the reference value PA2 (that is, the intersection between the characteristic line LA and the vertical axis), and these are stored along with the characteristic line LA in the memory component 12 ahead of time. The stored data need not be the measurement values for the reference value PA1 and the reference value PA2 themselves, and may be other numerical values that can be found by computation. For instance, they may be the values of the slope and the intercept of the characteristic line LA (=the reference value PA2), or they may be measurement values at two or more other points, which are different from the reference value PA1 and the reference value PA2.

Then, the determination of the reference point P1 is performed in Check A, and of reference point P2 in Check B.

First, in Check A, it is determined how much the present characteristics of the measurement component 9 are offset (how much they vary) from the characteristic line LA from the time of manufacture, at the reference point P1 (75 kΩ).

Figure 4:
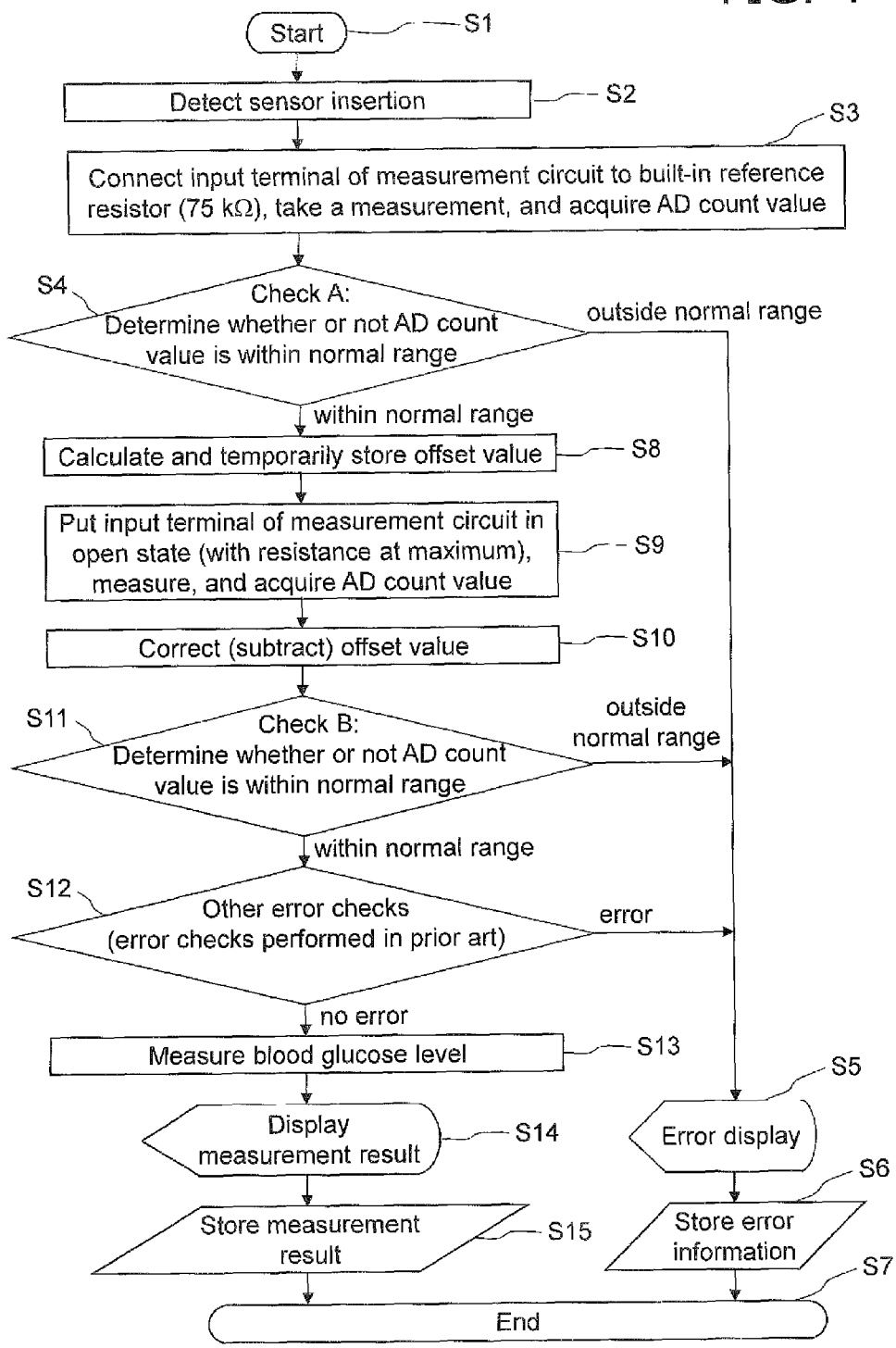
FIG. 4 is an operational flowchart of the biological sample measurement device in the first embodiment of the present invention.

More specifically, the controller 11 turns off the switch 14 of the switching component 10 and turns on the switch 15, so that the input side of the measurement component 9 is connected to the reference resistor 16 (75 kΩ), and the measurement component 9 measures the reference resistance 16 and finds the measurement value PB1 (AD count value) (step S3 in FIG. 4).

Under normal circumstances, the measurement value PB1 is the same as the reference value PA1, but if the AD conversion circuit (not shown) of the measurement component 9 or the like should be affected by some external factor such as temperature drift caused by the temperature in the measurement state, then the value will be offset from the reference value PA1 at the time of manufacture, as shown in FIG. 3.

Here, an abnormality determination component 18 of the controller 11 determines whether or not the measurement value PB1 is within the normal range (first reference range) defined by the magnitude of the threshold A1 above and below the reference value PA1 (step S4 in FIG. 4).

If the measurement value PB1 should be outside the normal range, and the present characteristics of the measurement component 9 differ from the characteristics at the time of manufacture and proper measurement is impossible, then the controller 11 will give a display on the display component 6 of "Meter malfunction" "Contact retailer. 1-800-123-4567," for example, thereby notifying the user that the measurement device has malfunctioned and prompting the user to contact the retailer or customer service (step S5 in FIG. 4).

After this, the controller 11 stores specific error information (such as the error details and the date and time it occurred) in the memory component 12 (step S6 in FIG. 4), and ends the processing without switching to measurement mode (step S7 in FIG. 4).

In contrast, if the measurement value PB1 is within the normal range, the reference value PA1 is subtracted from the measurement value PB1 to calculate the offset value, and this offset value is temporarily stored in the memory component 12 (step S8 in FIG. 4).

Thus, in Check A, the switching component 10 connects the input side of the measurement component 9 to the reference resistor 16 to find the first measurement value PB1, and determines whether or not this first measurement value PB1 is within the first reference range stored in the memory component 12.

Then, Check B is carried out.

In Check B, it is determined whether or not the slope indicating the characteristics of the measurement component 9 is the same as the slope of the characteristic line LA at the time of manufacture, at the reference point P2 (∞Ω, that is, a state in which the input side of the measurement component 9 is open).

More specifically, the controller 11 turns off the switch 14 of the switching component 10 and turns off the switch 15, so that the input side of the measurement component 9 is in an open state, and the measurement component 9 takes a measurement in this open state and finds the measurement value PB2 (AD count value) (step S9 in FIG. 4).

Accordingly, a line connecting the measurement value PB1 measured for the reference resistor 16 and this measurement value PB2 becomes the characteristic line LB representing the present characteristics of the measurement component 9.

It is determined whether or not the slope of this characteristic line LB is the same as the slope of the characteristic line LA at the time of manufacture.

More specifically, the controller 11 corrects (subtracts) this measurement value PB2 with the offset value found in Check A temporarily stored in the memory component 12, and finds the measurement value PB2*a* (step S10 in FIG. 4).

The abnormality determination component 18 of the controller 11 then determines whether or not the corrected measurement value PB2*a* is within the normal range (second reference range) defined by the magnitude of the threshold A2 above and below the reference value PA2 (step S11 in FIG. 4).

As shown in FIG. 3, if the measurement value PB2*a* is within the normal range, then when the present characteristic line LB is corrected (subtracted) with an offset value, it will either coincide with the characteristic line LA at the time of manufacture, or it will fall within the normal range. That is, the state at this time is such that the slope of the characteristic line LB is the same, or substantially the same, as the slope of the characteristic line LA at the time of manufacture, and the measurement component 9 is currently in a state of being offset from the characteristics at the time of manufacture, but maintains the characteristics at the time of manufacture. That is, there is currently no abnormality in the measurement component 9, and the controller 11 determines that blood glucose level measurement can be performed.

Thus, in Check B, the switching component 10 puts the input side of the measurement component 9 in an open state, the second measurement value PB2*a* is found, and it is determined whether or not this second measurement value PB2*a* is within the second reference range stored in the memory component 12.

If the measurement value PB2*a* is outside the normal range, then the slope of the characteristic line LB will be different from the slope of the characteristic line LA at the time of manufacture, that is, the present characteristics of the measurement component 9 will be different from the characteristics at the time of manufacture, and proper measurement will be considered impossible, so the controller 11 carries out steps S5 and S6 in FIG. 4, and ends the processing without switching to measurement mode (step S7 in FIG. 4).

In contrast, if the measurement value PB2*a* is within the normal range, Check B ends normally (step S11 in FIG. 4), and other error checks prior to measurement (error checks that are performed in prior art, such as an ambient temperature check, a hardware operation check, and a check of the memory component 12) are performed (step S12 in FIG. 4), after which the controller 11 switches to measurement mode. If an error occurs in step S12 in FIG. 4, the processing of steps S5 to S7 in FIG. 4 are carried out and measurement is ended.

After this, in measurement mode, the controller 11 switches on the switch 14 of the switching component 10 and switches off the switch 15, so that the input side of the measurement component 9 is connected to the sensor mounting component 4, and a message of "Measurement preparation complete. Deposit blood on sensor." is displayed on the display component 6. When blood is then deposited on the blood glucose level sensor 2, normal blood glucose level measurement is carried out (step S13 in FIG. 4).

Finally, the controller 11 displays the measured blood glucose level on the display component 6 (step S14 in FIG. 4), stores the blood glucose level in the memory component 12 (step S15 in FIG. 4), and ends the measurement (step S7 in FIG. 4).

Figure 5:
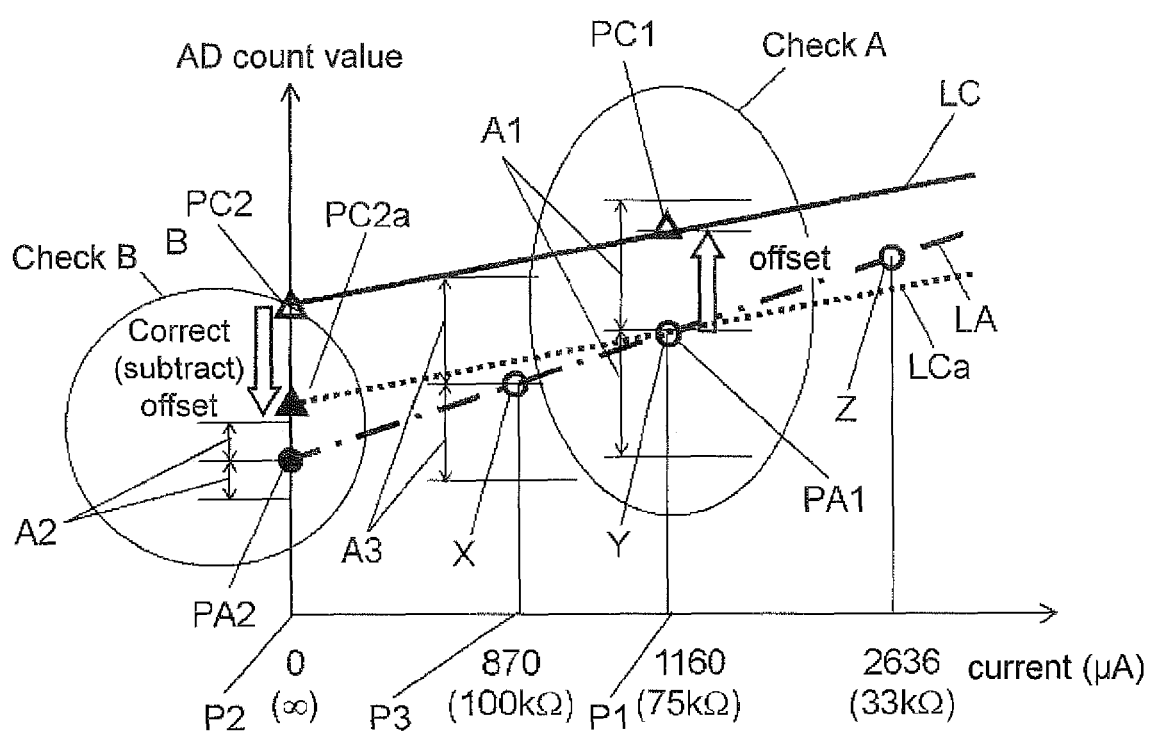
FIG. 5 is a characteristic graph of measurement values obtained with the biological sample measurement device in the first embodiment of the present invention.

As regards Check B in the measurement preparation mode in step S11 in FIG. 4, there are cases where the AD conversion circuit (not shown) and so forth of the measurement component 9, for example, have undergone an impact when the measurement device is dropped, or the measurement component 9 has been affected by external factors such as the degradation of parts through use over time. When this happens, as shown in FIG. 5, the measurement value PC1 (resistance of 75 kΩ) in Check A falls within the normal range defined by the threshold A1, but the measurement value PC2a in Check B (a value obtained by correcting the measurement value PC2 in an open state in steps S8 to S10 in FIG. 4) is outside the normal range defined by the threshold A2 with respect to the reference value PA2.

At this time, the slope of the characteristic line LC connecting the measurement value PC1 in Check A and the measurement value PC2 in Check B is different from the slope of the characteristic line LA at the time of manufacture, and in this state, even if the characteristic line LC is corrected with an offset value to obtain a characteristic line LCa, this characteristic line LCa will still not coincide with the characteristic line LA at the time of manufacture. Accordingly, when the blood glucose level sensor 2 is mounted and the blood glucose level is measured, the correct blood glucose level will not be obtained.

At this point, the controller 11 determines that the measurement component 9 is not currently maintaining the characteristics it had at the time of manufacture, the error processing of steps S5 and S6 in FIG. 4 is carried out, and subsequent measurement of the blood glucose level is halted (step S7 in FIG. 4).

As described above, in this embodiment, measurement is performed at two points, namely, the reference point P1 (75 kΩ) and the reference point P2 (∞Ω), in order to determine whether or not there is an abnormality in the measurement device, and the current characteristic line LB of the measurement component 9 is found from the measurement values at these two points. Then, the deviation and the difference in slope between the current characteristic line LB and the characteristic line LA at the time of manufacture are determined at the above-mentioned two points. Based on the determination at these two points, the controller 11 confirms that the measurement component 9 currently maintains the characteristics it had at the time of manufacture, that is, that there is no abnormality in the measurement component 9.

Consequently, it can be determined that there is currently no abnormality in the measurement component 9 prior to performing actual measurement.

That is, each time the blood glucose level sensor 2 is mounted to the sensor mounting component 4, it can be determined whether or not there is an abnormality in the measurement device, merely by mounting the blood glucose level sensor 2, without having to take time to mount a dedicated management chip ahead of time as was done in the past, and as a result, a biological sample measurement device that is more convenient to use can be provided.

In this embodiment, in order to determine whether or not there is an abnormality in the measurement device, as discussed above, measurement and confirmation are performed at two points (a plurality of points), namely, the reference point P1 (75 kΩ, that is, the reference resistor 16) and the reference point P2 (∞Ω, that is, when the input side of the measurement component 9 is in an open state).

Specifically, measurement and confirmation of one of the measurement points are performed in an open state, as at reference point P2 (∞Ω). Therefore, a configuration provided with a single reference resistor allows measurement and confirmation to be performed at two points, so it can be determined whether or not there is an abnormality in the measurement device with a simple configuration.

Furthermore, in this embodiment, the normal range (second reference range) defined by the threshold A2 in Check B is smaller than the normal range (first reference range) defined by the threshold A1 in Check A. Therefore, the operation of the measurement device can be evaluated more accurately.

Specifically, if there is influence from external factors, such as temperature drift caused by the temperature in the measurement state, as discussed above, the measurement value of the measurement component 9 will be temporarily offset, but as discussed above, this offset state can be corrected by finding an offset value. Therefore, in Check A the normal range defined by the threshold A1 is set larger. This accommodates a wider range of external factors such as temperature drift.

In contrast, in Check B, the normal range defined by the threshold A2 is set smaller. Consequently, the slope of the characteristic line LC is closely compared to the slope of the characteristic line LA at the time of manufacture. That is, as discussed above, if the slope of the present characteristic line LC is different from the slope of the characteristic line LA at the time of manufacture in the measurement component 9, the correct blood glucose level can no longer be found, so this slope is evaluated more strictly.

Therefore, while a wider range of external factors is accommodated in Check A, the correct blood glucose level can be obtained.

As a result, the operation of the measurement device can be evaluated more accurately, and a biological sample measurement device that is more convenient to use can be provided.

Second Embodiment

In the first embodiment of the present invention, in order to determine whether or not there was an abnormality in the measurement device, as discussed above, measurement and confirmation were performed at two points, namely, the reference point P1 (75 kΩ, that is, the reference resistor 16) and the reference point P2 (∞Ω, that is, when the input side of the measurement component 9 is in an open state), and it was confirmed that there was no abnormality in the measurement component 9. Specifically, the salient feature was that measurement and confirmation were performed at two points (a plurality of points).

With the biological sample measurement device in the second embodiment of the present invention, instead of performing measurement and confirmation at the reference point P2 (∞Ω, that is, when the input side of the measurement component 9 is in an open state) as in the first embodiment, another reference point P3 (such as 100 kΩ) is provided, and measurement and confirmation are performed at the two points that are the reference point P1 and the reference point P2, as shown in FIGS. 3 and 5.

More specifically, as shown in FIG. 2, one side of a reference resistor 20 (resistance corresponding to the reference point P3; 100 kΩ) is connected via a switch 19 to the input side of the measurement component 9, and the other side of this reference resistor 20 is grounded.

The switch 19 constitutes the switching component 10 along with the switches 14 and 15, and each of these is connected to the controller 11 and is turned on and off individually by the controller 11. The memory component 12 stores the threshold A3 shown in FIGS. 3 and 5 as the normal range (third reference range) of the measurement value of the reference resistor 20 (100 kΩ).

With the above configuration, the controller 11 can use the switching component 10 to switch between connection of the input side of the measurement component 9 to the sensor mounting component 4, connection to the reference resistor 16 (75 kΩ), and the reference resistor 20 (100 kΩ).

Therefore, just as with the above-mentioned reference point P1 and reference point P2, measurement and confirmation can be performed at the reference point P1 and the reference point P3, and it can be determined whether or not there is an abnormality in the measurement device.

Specifically, in this embodiment, the following two checks are performed.

In the first check, the switching component 10 connects the input side of the measurement component 9 to the reference resistor 16 to find the first measurement value PB1, and it is determined whether or not this first measurement value PB1 is within the first reference range stored in the memory component 12.

In the second check, the switching component 10 connects the input side of the measurement component 9 to the second reference resistor 20 to find the third measurement value PB3, and it is determined whether or not this third measurement value PB3 is within the third reference range stored in the memory component 12.

INDUSTRIAL APPLICABILITY

The present invention is expected to find wide application as a biological sample measurement device for measuring biological information, such as blood glucose levels from blood.

The invention claimed is:

1. A biological sample measurement device comprising:
a main body case including a sensor mounting component;
a measurement component including an input side, the measurement component connected to the sensor mounting component;
a detector configured to detect a mounting of a sensor to the sensor mounting component;
a processor connected to the measurement component and the detector, the processor including a measurement preparation mode and a measurement mode,
the processor programmed to:
perform a Check A and a Check B, Check B being different from Check A in the measurement preparation mode, determine whether the measurement component is normally able to measure a biological sample when the detector detects the mounting of the sensor to the sensor mounting component or when power for the biological sample measurement device is turned on,
perform a measurement of the biological sample in the measurement mode when it is determined that a proper measurement is possible in the Check A and the Check B
and
connect the input side of the measuring component to the sensor mounting component when the processor determines that there is no abnormality in the measurement preparation mode;
a memory component connected to the processor, the memory component including a first reference range and a second reference range;
Check A occurs in a state where the input side of the measurement component is connected by a switching component to a first reference resistor, the measurement component measures a first reference resistance and finds a first measurement value;
the processor determines whether or not the first measurement value is within a first reference range stored in the memory component;
the processor determines proper measurement is impossible if the first measurement value should be outside the first reference range;
Check B occurs in a state where the switching component puts the input side of the measurement component in an open state;
the measurement component measures in the open state and finds a second measurement value;
the processor determines whether or not the second measurement value is within a second reference range stored in the memory component;
the processor determines proper measurement is impossible if the second measurement value should be outside the second reference range;
the switching component connected to the input side of the measurement component, the first reference resistor, and the sensor mounting component;
the switching component configured to switch between at least a first state, a second state, and a third state, wherein all three states are different from each other,
the first state connecting the input side of the measurement component to the first reference resistor,
the second state connecting the input side of the measurement component to the sensor mounting component,
the third state being the open state;
the processor is further programmed to perform Check A while the switching component is in the first state; and
the processor is further programmed to perform Check B while the switching component is in the third state.

2. The biological sample measurement device according to claim 1, wherein:
after performing the determination of Check A, the processor is further programmed to find an offset value from the first measurement value and a reference value within the first reference range, and
the determination of Check B further includes correcting the second measurement value with the offset value before determining whether the second measurement value is within the second reference range.

3. The biological sample measurement device according to claim 1, wherein:
the second reference range is smaller than the first reference range.

4. A biological sample measurement device comprising:
a main body case including a sensor mounting component;
a measurement component including an input side, the measurement component connected to the sensor mounting component;
a detector configured to detect a mounting of a sensor to the sensor mounting component;
a processor connected to the measurement component and the detector, the processor including a measurement preparation mode and a measurement mode,
the processor programmed to:
perform a Check A and a Check B, Check B being different from Check A in the measurement preparation mode, determine whether the measurement component is normally able to measure a biological sample when the detector detects the mounting of the sensor to the sensor mounting component or when power for the biological sample measurement device is turned on,
perform a measurement of the biological sample in the measurement mode when it is determined that a proper measurement is possible in the Check A and the Check B
and
connect the input side of the measuring component to the sensor mounting component when the processor determines that there is no abnormality in the measurement preparation mode;
a memory component connected to the processor, the memory component including a first reference range and a third reference range;

Check A occurs in a state where the input side of the measurement component is connected by the switching component to a first reference resistor;
the measurement component measures a first reference resistance and finds a first measurement value;
the processor determines whether or not the first measurement value is within a first reference range stored in the memory component;
the processor determines proper measurement is impossible if the first measurement value should be outside the first reference range;
Check B occurs in a state where the input side of the measurement component is connected by the switching component to a second reference resistor,
the measurement component measures a second reference resistance and finds a third measurement value,
the processor determines whether or not the third measurement value is within a third reference range stored in the memory component,
the processor determines proper measurement is impossible if the third measurement value should be outside a third reference range;
the switching component connected to the input side of the measurement component, the first reference resistor, the second reference resistor, and the sensor mounting component;
the switching component configured to switch between at least a first state, a second state, and a third state, wherein all three states are different from each other,
the first state connecting the input side of the measurement component to the first reference resistor,
the second state connecting the input side of the measurement component to the sensor mounting component,
the third state connecting the input side of the measurement component to the second reference resistor;
the processor is further programmed to perform Check A while the switching component is in the first state; and
the processor is further programmed to perform Check B while the switching component is in the third state.

* * * * *